(12) United States Patent
Chakeres

(10) Patent No.: US 6,921,406 B1
(45) Date of Patent: Jul. 26, 2005

(54) STEREOTACTIC APPARATUS AND METHODS

(75) Inventor: Donald W. Chakeres, Dublin, OH (US)

(73) Assignee: The Ohio State University, Columbus, OH (US)

( * ) Notice: Subject to any disclaimer, the term of this patent is extended or adjusted under 35 U.S.C. 154(b) by 461 days.

(21) Appl. No.: 10/125,864

(22) Filed: Apr. 19, 2002

Related U.S. Application Data

(60) Provisional application No. 60/284,813, filed on Apr. 19, 2001.

(51) Int. Cl.[7] ............................................. A61B 19/00
(52) U.S. Cl. ..................................... 606/130; 600/429
(58) Field of Search ............................... 600/414, 417, 600/426, 429; 606/97, 130

(56) References Cited

U.S. PATENT DOCUMENTS

| | | |
|---|---|---|
| 4,551,678 A | 11/1985 | Morgan et al. |
| 4,583,538 A | 4/1986 | Onik et al. |
| 4,618,978 A | 10/1986 | Cosman |
| 4,638,798 A | 1/1987 | Sheldon et al. |
| 4,722,336 A | 2/1988 | Kim et al. |
| 4,750,487 A | 6/1988 | Zanetti |
| 5,030,223 A | 7/1991 | Anderson et al. |
| 5,053,042 A | 10/1991 | Bidwell |
| 5,142,559 A | 8/1992 | Wielopolski et al. |
| 5,147,372 A | 9/1992 | Nymark et al. |
| 5,263,956 A | 11/1993 | Nobles |
| 5,309,913 A | 5/1994 | Kormos et al. |
| 5,383,454 A | 1/1995 | Bucholz |
| 5,426,685 A | 6/1995 | Pellegrino et al. |
| 5,437,280 A | 8/1995 | Hussman |
| 5,447,154 A | 9/1995 | Cinquin et al. |
| 5,499,989 A | 3/1996 | LaBash |

(Continued)

FOREIGN PATENT DOCUMENTS

| | | |
|---|---|---|
| DE | 3937052 | 5/1990 |
| EP | 0386936 | 2/1990 |
| EP | 0832611 | 4/1998 |
| WO | WO 9522297 | 8/1995 |
| WO | WO 9610368 | 4/1996 |

OTHER PUBLICATIONS

Orel et al., Staging of Suspected Breast Cancer: Effect of MR Imaging and MR-guided Biopsy, Radiology 1995; 196: 115-122.

Stelling, Breast Cancer Staging with Contrast Material-Enhanced MR Imaging: Should it Change Patient Treatment?, Radiology 1995; 196:16-18.

Mumtaz et al., Laster Therapy for Breast Cancer: MR Imaging and Histophathologic Correclation, Radiology 1996; 200: 651-658.

Orel et al., MR Imaging-Guided Localization and Biopsy of Breast Lesions: Initial Experience, Radiology 1994: 193: 97-102.

*Primary Examiner*—Julian W. Woo
*Assistant Examiner*—Sarah Webb
(74) *Attorney, Agent, or Firm*—Standley Law Group LLP

(57) ABSTRACT

The present invention includes stereotactic vectors involving no electronic components. The invention also includes machines or instruments using those aspects of the invention. The present invention also includes methods and processes using the devices of the present invention.

20 Claims, 10 Drawing Sheets

U.S. PATENT DOCUMENTS

| | | |
|---|---|---|
| 5,628,315 A | 5/1997 | Vilsmeier et al. |
| 5,678,549 A | 10/1997 | Heywang-Koebrunner et al. |
| 5,690,108 A | 11/1997 | Chakeres |
| 5,830,219 A | 11/1998 | Bird et al. |
| 5,913,863 A | 6/1999 | Fischer et al. |
| 5,971,998 A | 10/1999 | Russell et al. |
| 6,159,221 A | 12/2000 | Chakeres |
| 6,261,299 B1 | 7/2001 | Chakeres |

…

STEREOTACTIC APPARATUS AND METHODS

This application claims the benefit of U.S. Provisional Patent Application No. 60/284,813, filed on Apr. 19, 2001, which is incorporated herein by reference.

TECHNICAL FIELD OF THE INVENTION

This invention relates generally to apparatus and methods useful in scientific research and interventional medicine, and useful in the visualization and analysis of organic tissues and bodies; and to research into the cause and symptoms of disease, its diagnosis and treatment. The invention particularly concerns apparatus which may be advantageously utilized by a researcher, physician or health care professional, in cooperation with types of medical imaging equipment, such as computed tomography (CT) imaging equipment or magnetic resonance (MR) imaging equipment, plain film or fluoroscopy. The invention may be utilized to conveniently and accurately aid in timely (real time), manually, truly, and physically accomplishing the steps of locating, vectoring, and inserting an object such as a probe or other needle-like medical device at, toward, and in a patient's targeted anatomic feature.

BACKGROUND OF THE INVENTION

This invention relates to a stereotactic device for use with imaging apparatus, such as magnetic resonance imaging ("MRI"), CT, or fluoroscopic apparatus, useful in the visualization and analysis of organic tissues and bodies, and to research into the cause and symptoms of disease, its diagnosis and treatment.

Many stereotactic devices for imaging are currently available. Despite the incredible power of many existing imaging technologies, surprisingly few procedures are actually done using these technologies in a routine clinical setting using any type of stereotactic assistance. There are several reasons for the lack of general acceptance of these devices in existing markets.

Most of these systems are expensive. Normally this expense cannot be justified in terms of usage or benefit for the large capital investment required. Physicians and hospitals are generally not prepared in today's economic climate to make a large investment for a system that may only be used intermittently and may become quickly outdated.

Most existing systems are electronic and use optical and computer interfaces. The majority of these systems do not function in a real-time setting, but rather use special post-processed acquired image information. This information is then used to direct the procedure at a different time and place.

Many of the systems are imager proprietary or dependent, so it is possible that only a few units may be able to use a specific technology. Though these systems claim to have very high real-space accuracy, in reality they have only limited real-space correlation since there is no live (real-time) imaging to confirm the progress of the procedure.

Most stereotactic units are complex and have multiple components. Some of the systems envelop the patient, such as through the use of head frames bolted directly to the skull. If there is any change in the components of such a rigid system at the time and place of the actual intervention, the previously obtained information that forms the basis for the intervention is no longer valid.

These systems also rely on gathering many images to direct the operation, rather than needing only a few. Because of this, the process can be very slow, since a large amount of data needs to be acquired to direct the process.

A number of existing stereotactic systems utilize fiducials that are placed on the patient or the stereotactic frame. These are image-conspicuous markers that are seen in the image space and in real-space. Utilizing this information, the virtual reality space depicted on the images is then fused with the real-space.

There are a number of devices that attach directly to the scanner, but these are generally cumbersome and have not been used extensively.

There are also a few systems that use very limited vector trajectories (of only a few angles). These are of little value since the limited number of approaches they provide to the target may not be enough to address the complicated anatomy, therapeutic devices, and goals of a variety of procedures.

Currently there are a number of rapid CT or MRI data acquisition systems available, but they have the disadvantages of being proprietary and of exposing the patient and operator to increased radiation dosage. These CT systems are analogous to fluoroscopy.

There are a few combined CT and fluoroscopic stereotactic systems. These have the potential to be very versatile, but they are complex proprietary systems. There are also a number of open magnet designs, but these are limited by vendor design. Critical information used to direct the procedure or intervention is based on artifacts from the needle or probe rather than on accurate real-time real-space information. The inherent imaging problems created by these artifacts limit the accuracy of these devices. The image quality of the fast imaging systems in general is not as good as routine imaging techniques.

FIG. 1 is a schematic of an enveloping frame that is used for head stereotactic systems of the prior art. The vertical lines 1 of the box represent the vertical struts, the horizontal lines 2 are crossing members used to define the section plane, the angled lines 3 represent cross-members, and the sphere 4 is the target. This frame is bolted or rigidly fixed to the patient and then imaged with many sections. The information gathered is used at a later time and place. Without real-time real-space confirmation during the intervention, there is no absolute confirmation that the previously determined plan is actually being correctly implemented.

FIG. 2 is a schematic of an image obtained from such a fixed frame rigid system. The vertical members 1 are seen at the corners of the square. The cross-members 3 are used to define the slice location and the target 4. There is no intuitive information that an operator can use to confirm that the information is accurate. Typically, a second system is used to actually execute the procedure at a later time with no real-time real-space confirmation of the previously obtained plan.

FIG. 3 shows an example of an MRI image 5 showing the use of a fixed frame stereotactic unit used for head imaging. The head 6 appears in the center of the image, with the target labeled in the left temporal bone. Also visible are the rods 7 (such as horizontal, vertical and cross-members 1, 2 and 3 shown in FIG. 2) surrounding the skull of the patient as a fixed device. The information is acquired by taking multiple images that must be post-processed.

There are a number of limitations to this type of device. The constituent support tubes are necessarily relatively large (in order to support the static arrangement), and thus cause a certain degree of inherent error in the system. The image shown is a single image that provides no real-time information that an operator might use during an image-monitored procedure. Also, a further error factor arises because the tubes are relatively distant from the target site, and the image itself is not without distortion, making the system distortion sensitive. Also, if the subject is moved then the system cannot be readily realigned.

A number of computer-based virtual reality systems' disadvantages have been mentioned. The most important of these is that they provide no real-time confirmation at the actual time of intervention. All of these systems use specially acquired post-processed images that assume the virtual reality of the previously obtained imaging information and the true reality at the time of the actual intervention are identical. These systems are expensive, large, and can only be used in select locations.

There remain problems associated with fast, open, and combined technology systems. All are expensive, vendor specific and, as such, are limited to only a few sites. They are such complicated systems that any minor problem can render them useless, such as if the batteries on an LED were to stop working. They have limited real-space accuracy since they have problems with partial volume averaging and other imaging artifacts. Using these systems it may be difficult to track more than one device being used at a time.

Accordingly, the criteria for an improved stereotactic device include:

1. Accuracy in the form of mm level control and live image confirmation.
2. Ability to make rapid adjustments (preferably by remote control), and the use of a single image.
3. Flexibility in the form of multiple dimension adjustability, and the accommodation of a wide variety of probes.
4. Intuitive use through clear, non-computer-generated interpretation of electronic image information.
5. Simple construction; a device that may be compact enough to fix the imager on the patient and inexpensively constructed, and may be of disposable materials.
6. Applicability independent of site and imaging device.

Accordingly, there remains a need for relatively inexpensive stereotactic devices that may be used with a wide variety of imaging systems for the performance of varied procedures, and that may be used with any number of invasive devices and techniques.

SUMMARY OF THE INVENTION

The present invention defines stereotactic vectors requiring no electronic components. The invention includes a stereotactic device comprising: (1) a frame portion having an opening defining an upper alignment plane; (2) a first planar member comprising a first pair of substantially parallel image-conspicuous lines, the first planar member having a first slot disposed between the first pair of substantially parallel image-conspicuous lines; and (3) a second planar member comprising a second pair of substantially parallel image-conspicuous lines, the second planar member having a second slot disposed a between the second pair of substantially parallel image-conspicuous lines; the first planar member overlying the second planar member such that the first pair of substantially parallel image-conspicuous lines forms an angle with the second pair of substantially parallel image-conspicuous lines, the first and second planar members adapted to move with respect to one another so as to be capable of providing an aperture, formed by the intersection of the first and second slots, at any position within the upper line plane.

The device may additionally comprise a lower plane portion comprising an image-conspicuous material defining at least one angle of about 53 degrees.

The first and second planar members are preferably interwoven through the first and second slots. The first pair of substantially parallel image-conspicuous lines may also be of a different width than the second pair of substantially parallel image-conspicuous lines.

The substantially parallel image-conspicuous lines may be selected from the group consisting of metal members, hollow polymeric members filled with an imager-conspicuous material, and polymeric members treated with an imager-conspicuous material.

The device may also comprise a sleeve or other support for housing the first and second planar members, the sleeve capable of attaching to the frame portion. The sleeve preferably contacts differing portions of the first and second planar members such that when the sleeve is pinched at certain locations, one of the planar members is locked in place and only the other planar member may be moved with respect to the sleeve.

The frame portion may be adapted to rotate the first and second planar members with respect to an axis perpendicular to said first and second planar members. The frame portion may additionally comprise a graduated position scale to indicate the degree of rotation of the first and second planar members.

The device may additionally comprise at least one remote activator to move the first and second planar members. The remote activator preferably comprises a device to measure its linear scaled movement, the device comprising: (1) a hollow sleeve, (2) a moveable member adapted to move within the sleeve (or hydraulic slide), and (3) an engaging member extending into the hollow sleeve a sufficient distance to engage the moveable member so as to permit the moveable member to be moved within the hollow outer sleeve by a motion of the engaging member, and the engaging member disposed with respect to the moveable member so as to permit the moveable member to be moved discrete distances within the hollow outer sleeve.

The lower plane portion may comprise a perforable material through which a medical instrument may be passed. The lower plane portion may additionally comprise a pair of adjacent angled patterns of an imager conspicuous material. The adjacent angled patterns preferably define an angle of approximately 53 degrees. The perforable material may additionally comprise a graduated linear distance position scale. The lower frame is generally not needed for fluoroscopy-type procedures.

The lower plane portion may additionally comprise an adhesive base portion. The lower plane portion may also be connected to an attachment band, drape material, or attachment band attached to a drape material.

Also included in the present invention is a method of placing a probe or defining a vector from outside a tissue into a target area located within the tissue using an imaging device, the target area being within reach of the probe from a targeting surface of the tissue, the method comprising: (1) establishing a lower plane substantially at the surface of the tissue, the lower plane comprising a lower vector point; (2) establishing an upper alignment plane above the surface of the tissue, the upper plane comprising: (I) a first planar member comprising a first pair of substantially parallel image-conspicuous lines, the first planar member having a first slot disposed between the first pair of substantially parallel image-conspicuous lines; (ii) a second planar member comprising a second pair of substantially parallel image-conspicuous lines, the second planar member having a second slot disposed between the second pair of substantially parallel image-conspicuous lines; the first planar member overlying the second planar member such that the first pair of substantially parallel image-conspicuous lines forms an angle with the second pair of substantially parallel image-conspicuous lines, the first and second planar members adapted to move with respect to one another so as to be capable of providing an aperture, formed by the intersection of the first and second slots, at different positions within the upper line plane, the aperture of a dimension through which at least a portion of a medical instrument may be passed; (3) if not so aligned, aligning the upper alignment plane such that the image plane of the imaging device is aligned perpendicular to the bisector of the angle formed by the substantially parallel image-conspicuous lines; (4) determining the position of the aperture with respect to the lower vector point of the lower plane; (5) adjusting the first and second planar members so as to form a vector containing the lower vector point, the aperture, and the target area; and (6) passing the probe along the vector to the target area.

The device and methods of the present invention may be used with any diagnostic or clinical imaging device, such as MRI, CT, radiographic or fluoroscopic devices. The device and methods of the present invention may also be used with industrial imaging devices in fields even outside of life sciences and medicine.

The device of the present invention is in part based on a unique image pattern that encodes exact dimensional information (e.g., in mm) on each image that is directly related to the identical dimensional positions (e.g., in mm) in real-time and 3D space. This means there is no need for computers or any other type of complex translation of the image information to utilize data in the real-time space of the image system.

In a real-time environment, the visual cues generated by the device-generated pattern lead the operator to an exact real-time space location without the need of special computer information. For example, if the operator is moving in the correct direction, the pattern displays the points moving toward the vector. If the operator is moving in the wrong direction, the points move away from the vector.

The pattern generated by devices of the present invention, in its preferred embodiment, is based on a specific geometric oddity. A triangle formed in a square has this property when the base of the triangle is the base of the square and the apex of the triangle is the midpoint of the top of the square. The triangle formed in this specific situation is a special isosceles triangle of about 53 degrees. The pattern of the preferred inventive device uses the limbs of this triangle. The limbs of the preferred device pattern are made of image conspicuous materials.

When the imaging section plane is parallel to the pattern it produces a set of unique imaging and real-space characteristics.

The true distance between the limbs of the device image conspicuous pattern as measured on the image is equal to the true distance from the intersection of the pattern limbs. There is no need for a computer to tell the operator when this occurs or for complex calculations. The slice location is encoded as a true linear measurement on the image.

The distance from a limb of the device's image conspicuous pattern to a vector line measured on the image can be used to define the same point in real-space on the device.

FIG. 4 shows examples of the stereotactic pattern generated by a device in accordance with one embodiment of the present invention.

The "V" shapes represent the device-generated pattern. The angle of the "V" shape should preferably be about 53 degrees.

The device pattern has a unique characteristic. The distance between the limbs (horizontal arrows 8) of the pattern measured on the image when the slice symmetrically crosses the pattern (parallel to the base of the triangle) is equal to distance from the intersection of the two limbs (i.e., the distance along vertical arrows 9). Note that independent of where the image slice crosses the pattern, the distance from the intersection of the two limbs is encoded on the image by the pattern being of an image conspicuous material. This relationship allows for immediate exact definition of the location of the section plane in real-space on the pattern using only this simple image information.

For instance, when using CT, each limb of the "V" may be made of an image conspicuous material such as wire. In the case of MRI, tubes (typically non-metallic; plastic) filled with contrast enhanced fluid may be used as pattern limbs. The pattern may also be drawn directly on the patient, or included on an imager transparent material attached to the patient, such as through the use of adhesives. Examples may include a piece of flexible material, such as Mylar, provided with an adhesive on one side and bearing an image conspicuous pattern (provided in the form of an attached image conspicuous object in the shape of the "V", or in the form of a printed design in the shape of the "V" in accordance with the present invention). Another example may be an adhesive strip, similar to an adhesive bandage, and provided with image conspicuous material members attached thereto, or an image conspicuous "V" pattern printed thereupon.

Thus, one of the fundamental features of the preferred device is that it provides a three-dimensional alignment template that resides at a distance from the identified target point without having the target point located within the space defined by the three-dimensional alignment template. This allows the three-dimensional alignment template to be repositioned and to function accurately even if the tissue or patient has moved.

Generally, devices in accordance with present invention may be accurate to within 1 or 2 units (i.e., mm or less) of the limits of the image resolution. These levels of accuracy may be achieved independent of the section thickness and orientation.

When an instrument is attached to a pattern device of the present invention, its position may be encoded independent of the slice thickness. Accordingly, partial volume artifact vector errors may be eliminated. The relationship of the instrument to the image may be encoded, a capability not possessed by known prior art devices.

In order to align the device and the section plane with sufficient accuracy and confidence, a device of the present invention may use its pattern to simultaneously encode the exact angle of alignment with the image plane in units that are printed on the pattern device for proper image section plane orientation. Based on the reading of these units, the operator may either rotate the device into alignment with the section plane or the plane may be rotated parallel to the device.

The ability of the device of the present invention to align the pattern to the image plane is possible because it is based on a number of unique mathematic and geometric relationships.

DETAILED DESCRIPTION OF THE PREFERRED EMBODIMENTS

Figure 1:
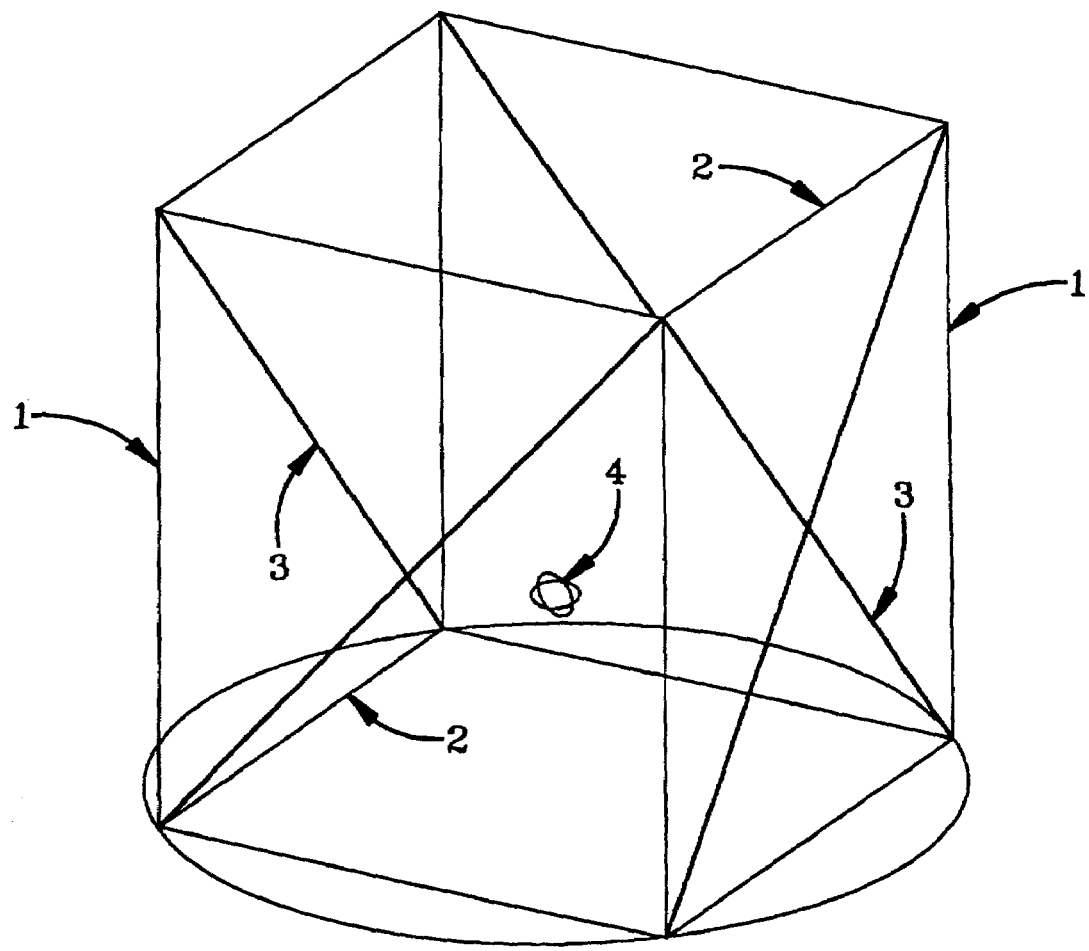
FIG. 1 is a schematic of an enveloping frame that is used for head stereotactic systems of the prior art.
Figure 2:
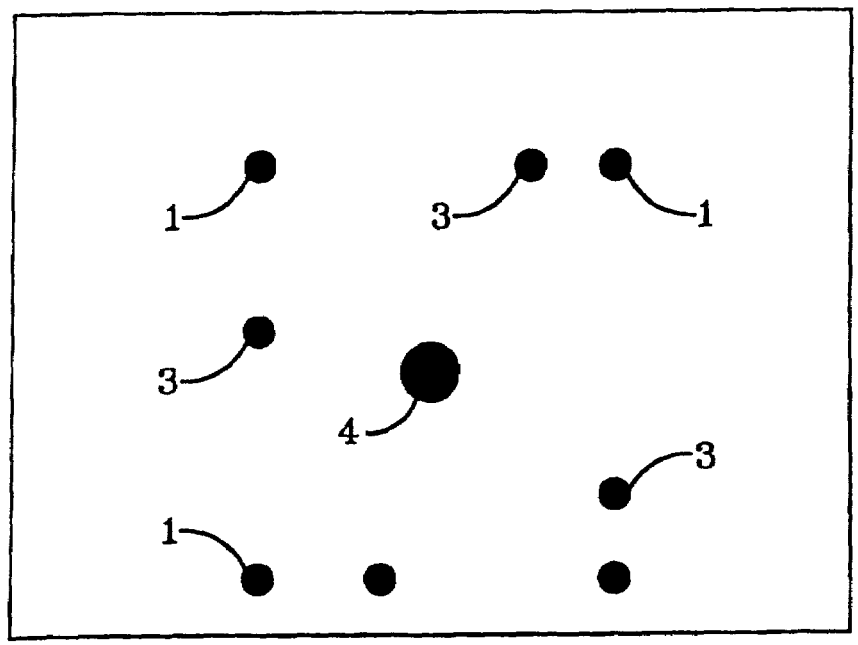
FIG. 2 is a schematic of an image obtained from a fixed frame rigid system in accordance with the prior art.
Figure 3:
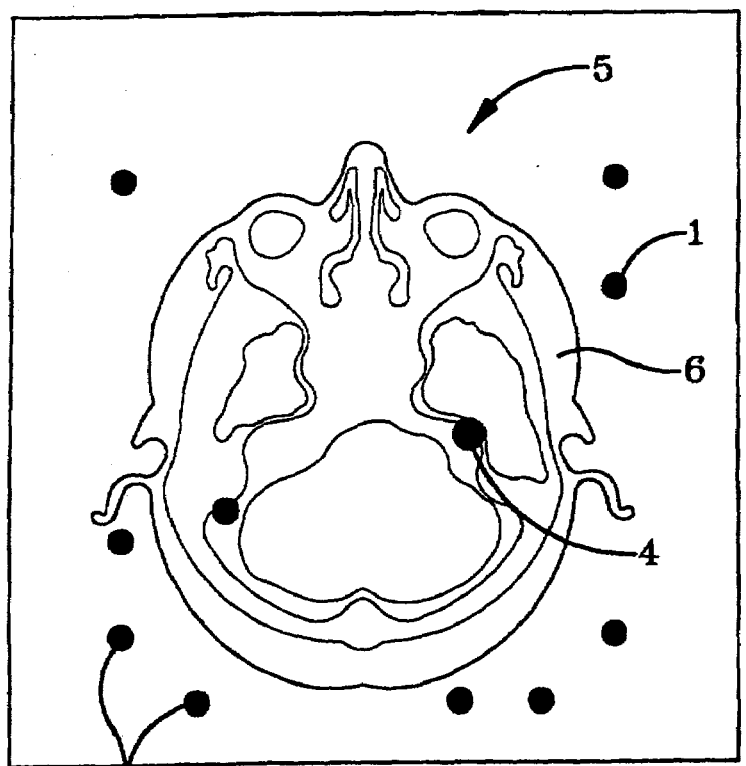
FIG. 3 shows an example of an MRI image showing the use of a fixed frame stereotactic unit used for head imaging in accordance with the prior art.
Figure 4:
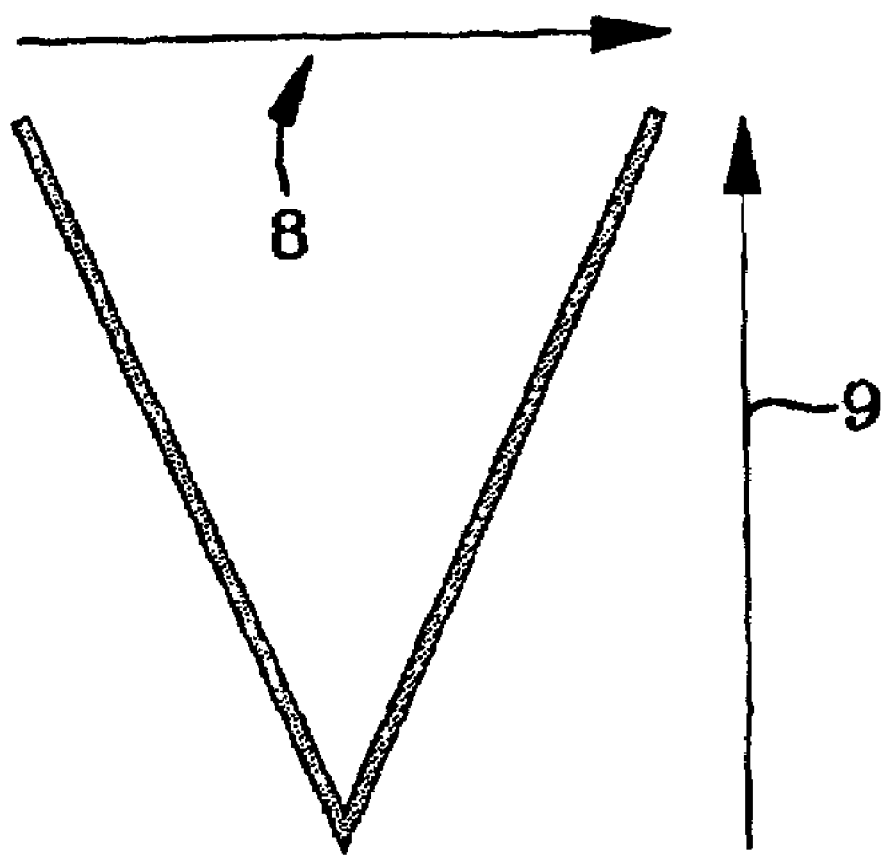
FIG. 4 shows examples of the stereotactic pattern generated by a device in accordance with one embodiment of the present invention.

In accordance with the foregoing summary of the invention, the following is a detailed description of a preferred embodiment of the invention, and is presently considered to be the best mode of the invention as applied.

The device of the present invention may be made of any combination of appropriate materials such as sterile, biocompatible materials (e.g., plastic, wire, tubes, catheters, diaphragms, etc.).

As described in more detail below, a preferred device of the present invention has three main components:
1. A lower plane portion that aligns to the image plane, and is directly attached to the target tissue, such as a patient's skin or other surface if needed. This component preferably has two "V" patterns with associated mm scale patterns. It also may have a rotation correction scale (V1–V2) printed on it. One of the "V" patterns may be removed to make the template smaller. This component defines the point at which the probe (i.e., instrument, light beam, etc.) enters the tissue. This component may also help the operator keep track of the position of the tissue or patient with respect to the imaging field. It may be directly attached to the patient, and is preferably very thin, typically about 3 mm maximum.
2. A frame portion, such as an adhesive attached structure that supports the upper plane portion and helps align the upper plane portion to the lower plane portion. This component may have an adhesive clear base, and may be molded to the patient's surface. For instance, it may be in the form of a circular sponge ring (5 mm thick) that engages the intermediate frame portion attached to the upper plane portion or other attachments such as a table. The upper plane portion may be turned in the lower frame portion allowing the operator to bring the upper plane portion parallel to the image plane. This component is placed in a location between the upper plane portion and the lower plane portion so that the chosen vector will be correct. In an alternative embodiment the lower plane portion may be integrated with the lower plane portion section plane.
3. An upper plane portion that supports/aligns the upper end of the probe (i.e., instrument, light beam, matter beam, etc.) away from the skin. For instance, in the case of a needle, it may be advanced into the device and held by it. The upper component has first and second planar members, each planar member having a pair of substantially parallel image-conspicuous lines, with a slot disposed between each pair of substantially parallel image-conspicuous lines. Each pair may have a different thickness and separation. The first planar member overlies the second planar member such that the first pair of substantially parallel image-conspicuous lines forms an angle with the second pair of substantially parallel image-conspicuous lines, the first and second planar members adapted to move with respect to one another so as to be capable of providing an aperture, formed by the intersection of the first and second slots, at different positions within the upper line plane. These angles are then used to orient the operator, to confirm the relationship to the image plane as well as confirm the location of the needle or probe.

In a preferred embodiment there are 4 parts as described in the drawings. The lower plane portion is directly attached to the target tissue to provide an entry point for a medical instrument to be passed. The second part, the intermediate base, is a clear plastic cylinder that is attached to the upper plane portion so as to support the "V" patterns with a slot. The upper plane portion has two planar members with substantially parallel image-conspicuous lines. These pairs of lines form adjustable "V" patterns, the area between the vertices of the "V" patterns forming an insertion point that actually supports the probe. This point moves as the planar members are moved back and forth with respect to one another.

The fourth part is the optional cable-catheter mechanism that moves the angled interwoven members longitudinally with respect to one another.

A fifth part may be an optional handle that can be manually moved or moved with a computer remote control mechanical system to adjust the component from a distance the exact required dimensions. This part may be provided with mm dimensions on it guiding the operator.

There are preferably two controls on the handle, one for each planar member. There may also be an optional control to control the rotation of the upper plane portion with respect to the lower plane portion.

Figure 5:
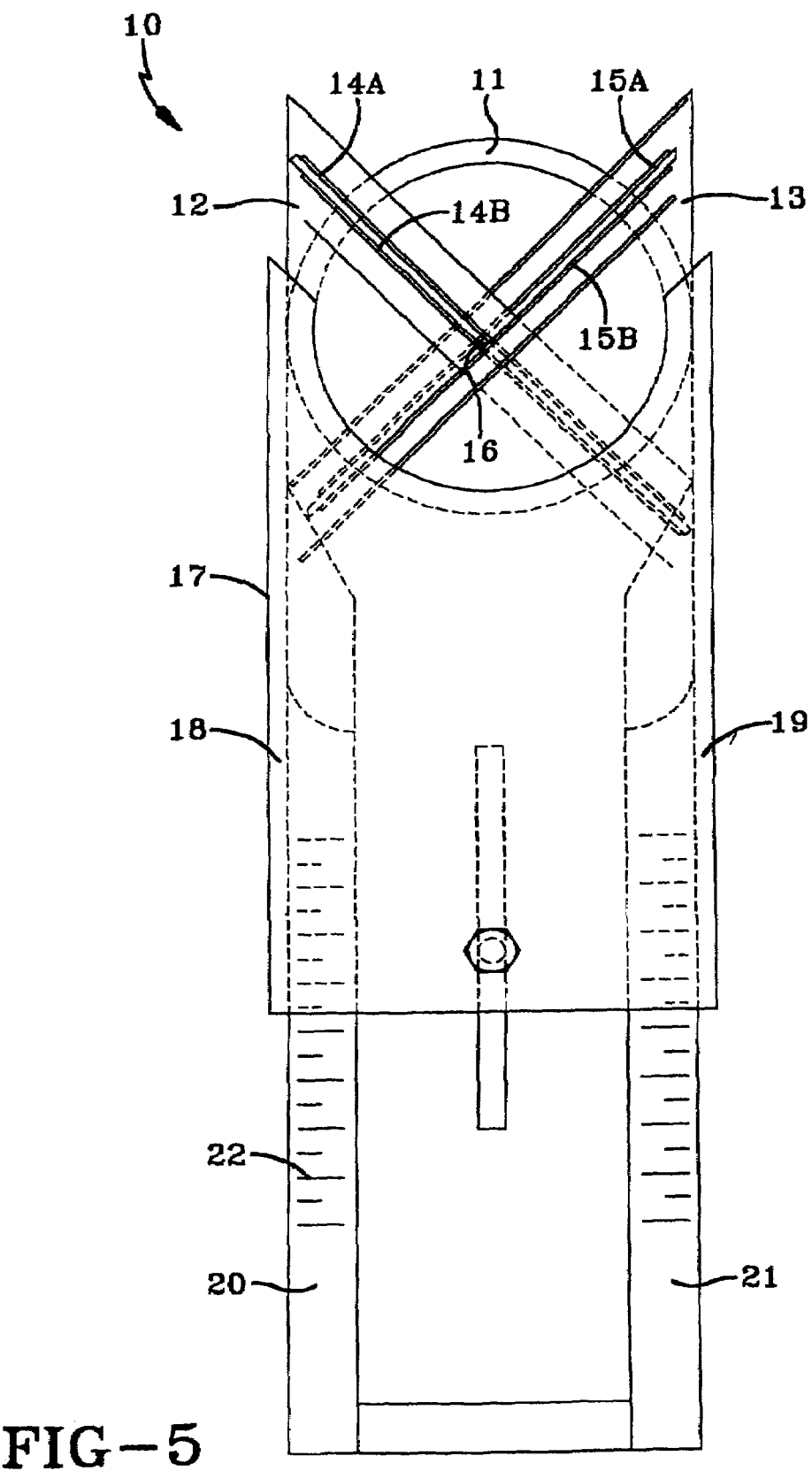
FIG. 5 is a top view of a stereotactic device that may be used in accordance with one embodiment of the present invention.

FIG. 5 shows a top view of a stereotactic device 10 in accordance with one embodiment of the present invention. FIG. 5 shows the intermediate frame portion 11 supporting the upper plane portion. The upper plane portion comprises the first planar member 12 and the second planar member 13. The first planar member 12 contains a first pair of image-conspicuous lines 14a and 14b. The second planar member contains a second pair of image-conspicuous lines 15a and 15b. A slot exists between each pair of image-conspicuous lines such that at the intersection of the slots an aperture 16 is formed, through which at least a portion of a medical instrument may be passed.

A flexible sleeve 17 is preferably contained in the device to control and restrain the movement of the first planar member 12 and the second planar member 13. The sleeve contains two pinch points 18 and 19. The first pinch point 18 may be used to lock the first planar member 12 in place while allowing the second planar member 13 to move. The second planar member should be appropriately shaped so that when the flexible sleeve 17 is pinched at the first pinch point 18 the second planar member is not restrained. A similar second pinch point 19 is used to restrain the second planar member 13 and allow movement of the first planar member 12.

When pinching the second pinch point 19, the first planar member may be moved by grasping the first member handle 20 and moving the first planar member the appropriate distance. The distance may be measured using an optional rule 22 on the handle 20. Similarly, a second member handle 21 exists to move the second planar member 13.

Figure 6:
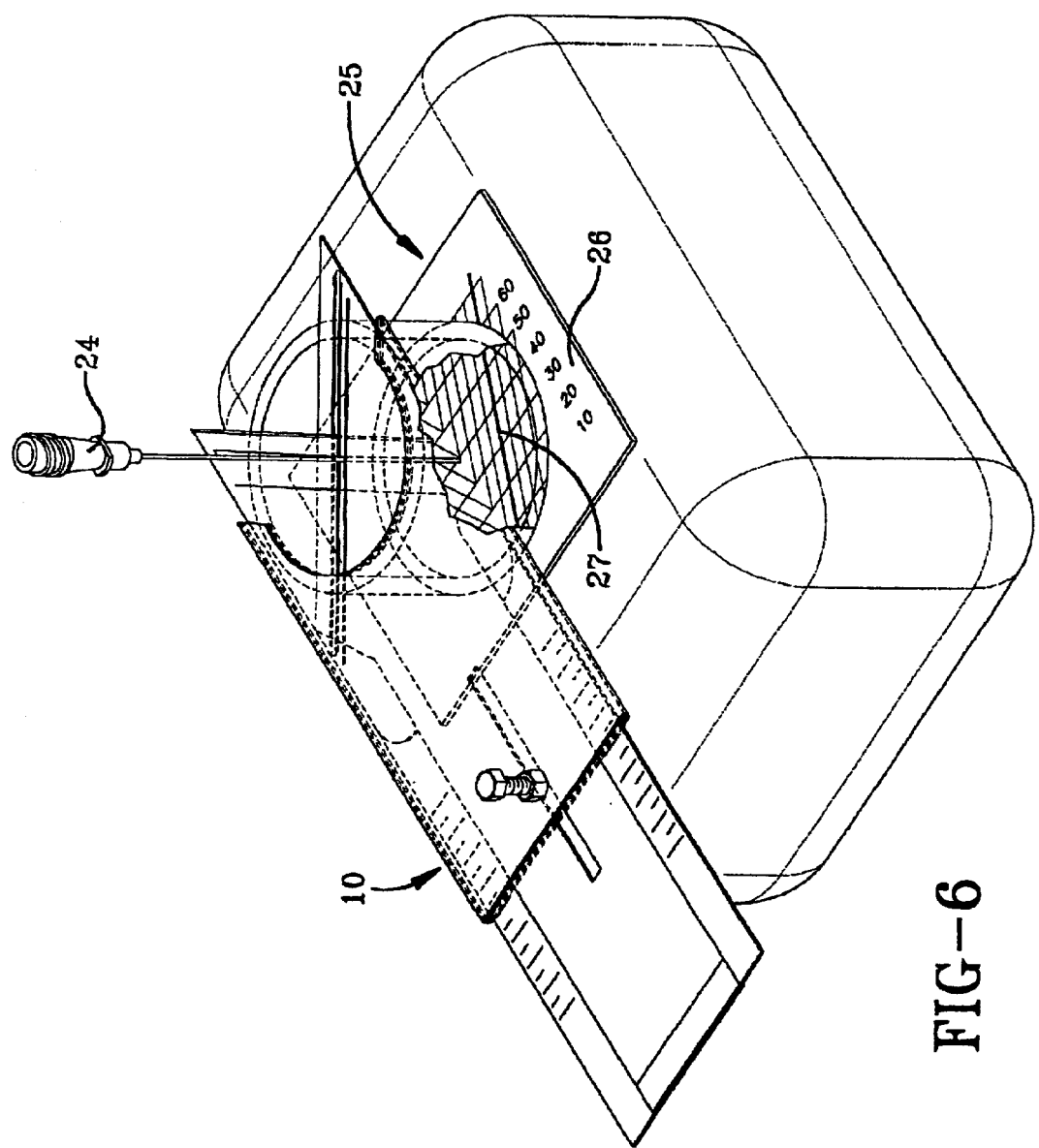
FIG. 6 is a perspective view of a medical probe inserted into a stereotactic device that may be used in accordance with one embodiment of the present invention.

FIG. 6 shows a medical probe 24 inserted into a preferred stereotactic device 10. The stereotactic device 10 is shown positioned on a 3-dimensional mass 28 representing an appropriate specimen for use with the device, such as a portion of a patient's body. The lower plane portion 25 of the device 10 is also shown. The lower plane portion 25 comprises a template 26 that preferably contains a pair of adjacent angled patterns of an imager conspicuous material. The adjacent angled patterns preferably define an angle of approximately 53 degrees. The lower plane portion preferably also comprises a linear distance position scale 27. The template 26 may be perforable such that at least a portion of a medical instrument may be passed through the template. The linear distance scale may be used to determine the insertion point on the lower plane of the medical instrument. This insertion point will then be used along with the entry point of the lesion to determine the necessary location of the aperture 16 in the upper alignment plane.

Figure 7:
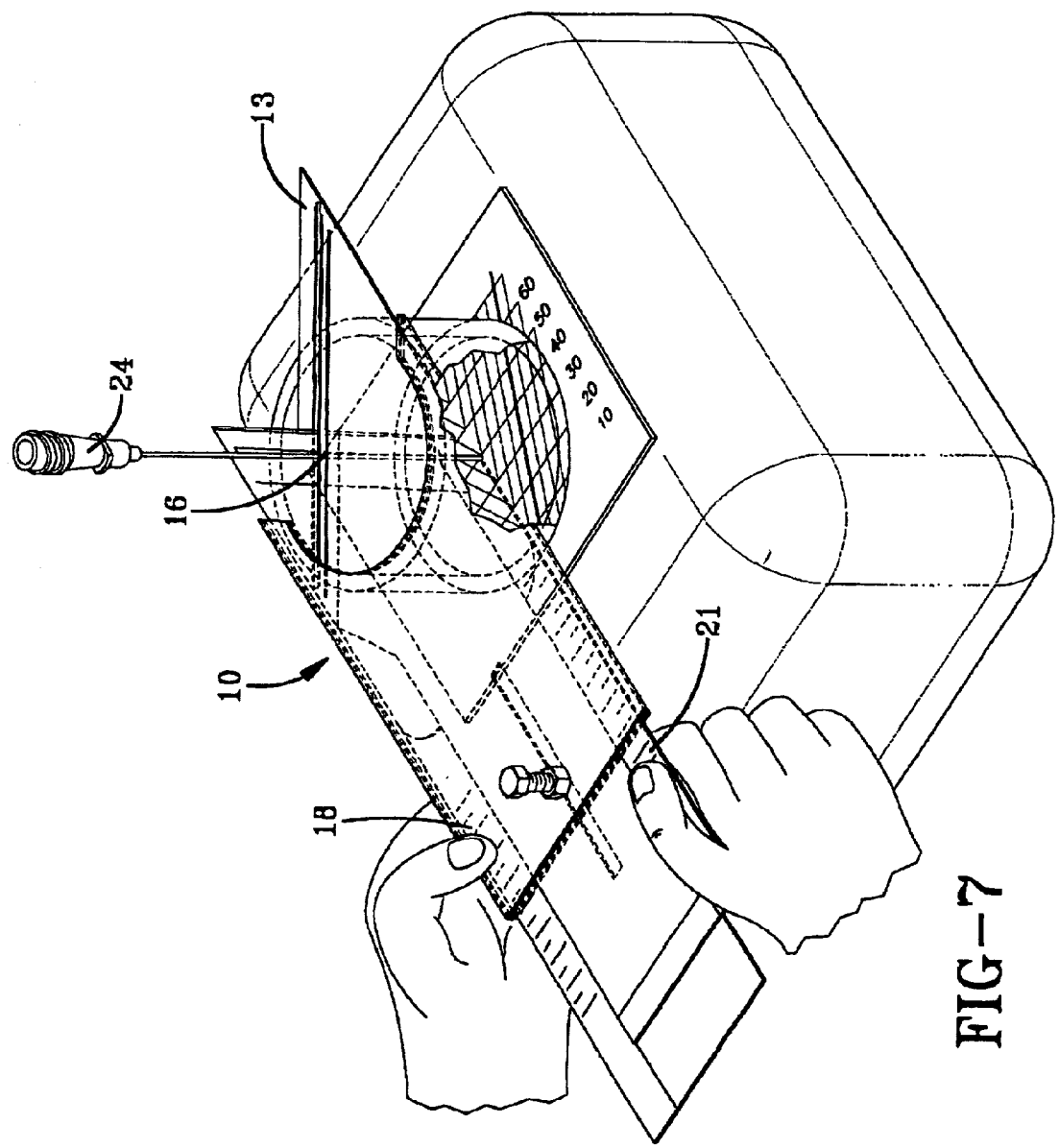
FIG. 7 is another view of a stereotactic device that may be used in accordance with one embodiment of the present invention.

FIG. 7 shows a person pinching the first pinch location 18 of a stereotactic device 10 of the present invention. The person can then use the second member handle 21 to move the second planar member 13, thereby moving the position of the aperture 16 in the upper alignment plane.

Figure 8:
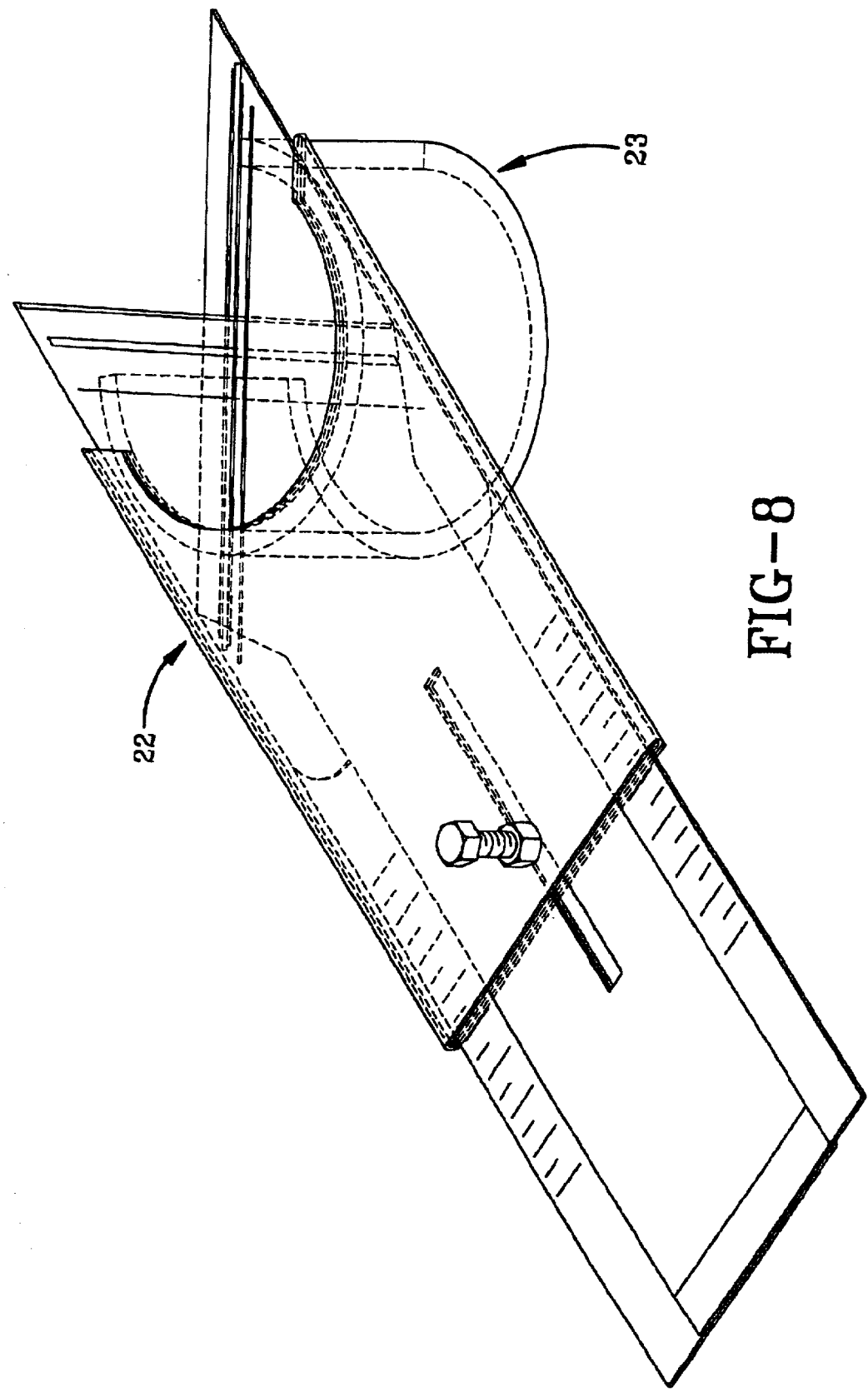
FIG. 8 is a top view of another stereotactic device that may be used in accordance with one embodiment of the present invention.

FIG. 8 shows an alternate embodiment of a stereotactic device 22 that may be used in accordance with one embodiment of the present invention. The intermediate frame portion 23 of this device 22 is not a close frame but is shown with an opening in the end of the device away from the handles. This allows removal of the device without removing the inserted medical device by breaking the membrane.

Figure 9:
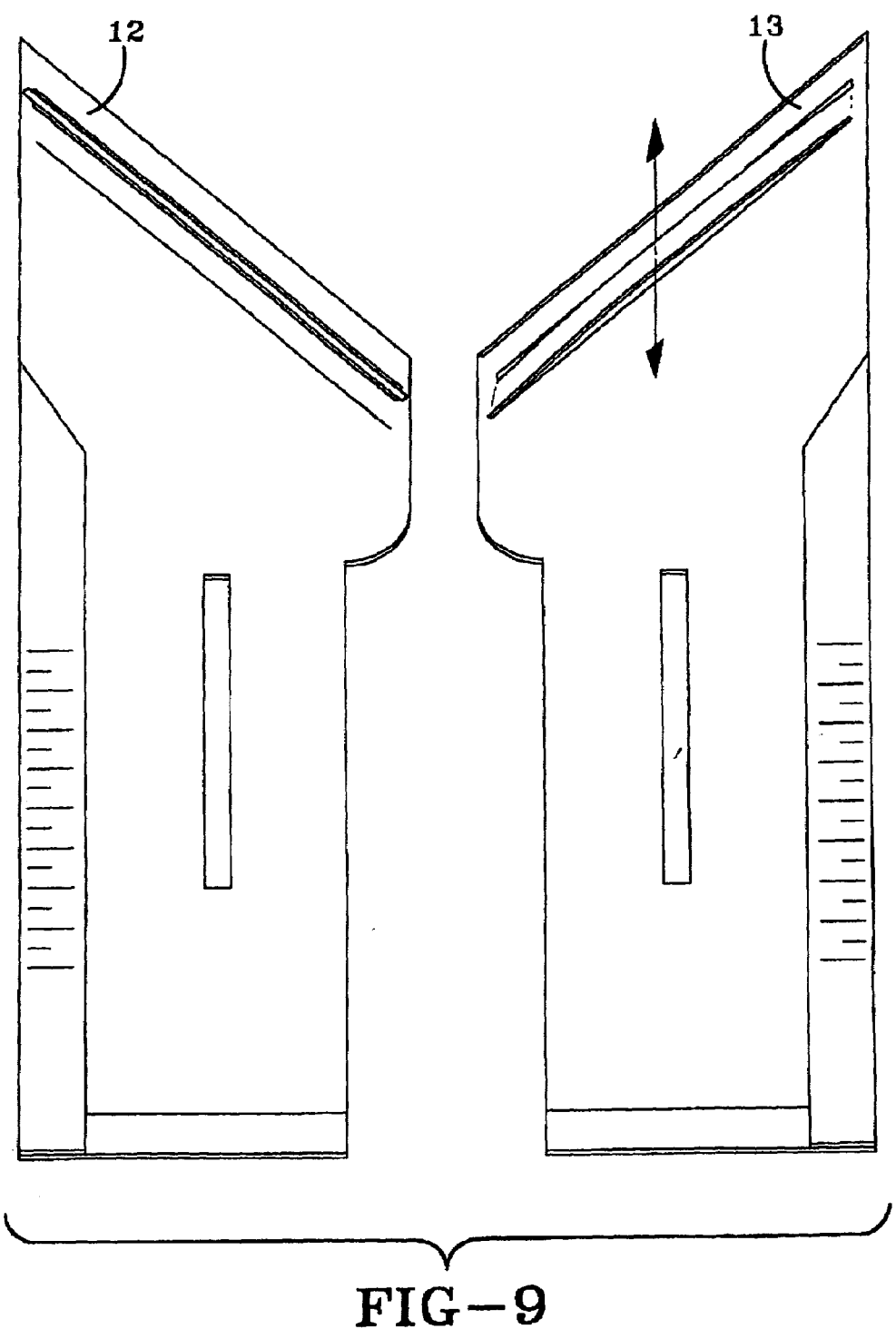
FIG. 9 is a top view of first and second planar members that may be used in accordance with one embodiment of the present invention.

FIG. 9 shows the preferred shapes of the first planar member 12 and the second planar member 13.

Figure 10:
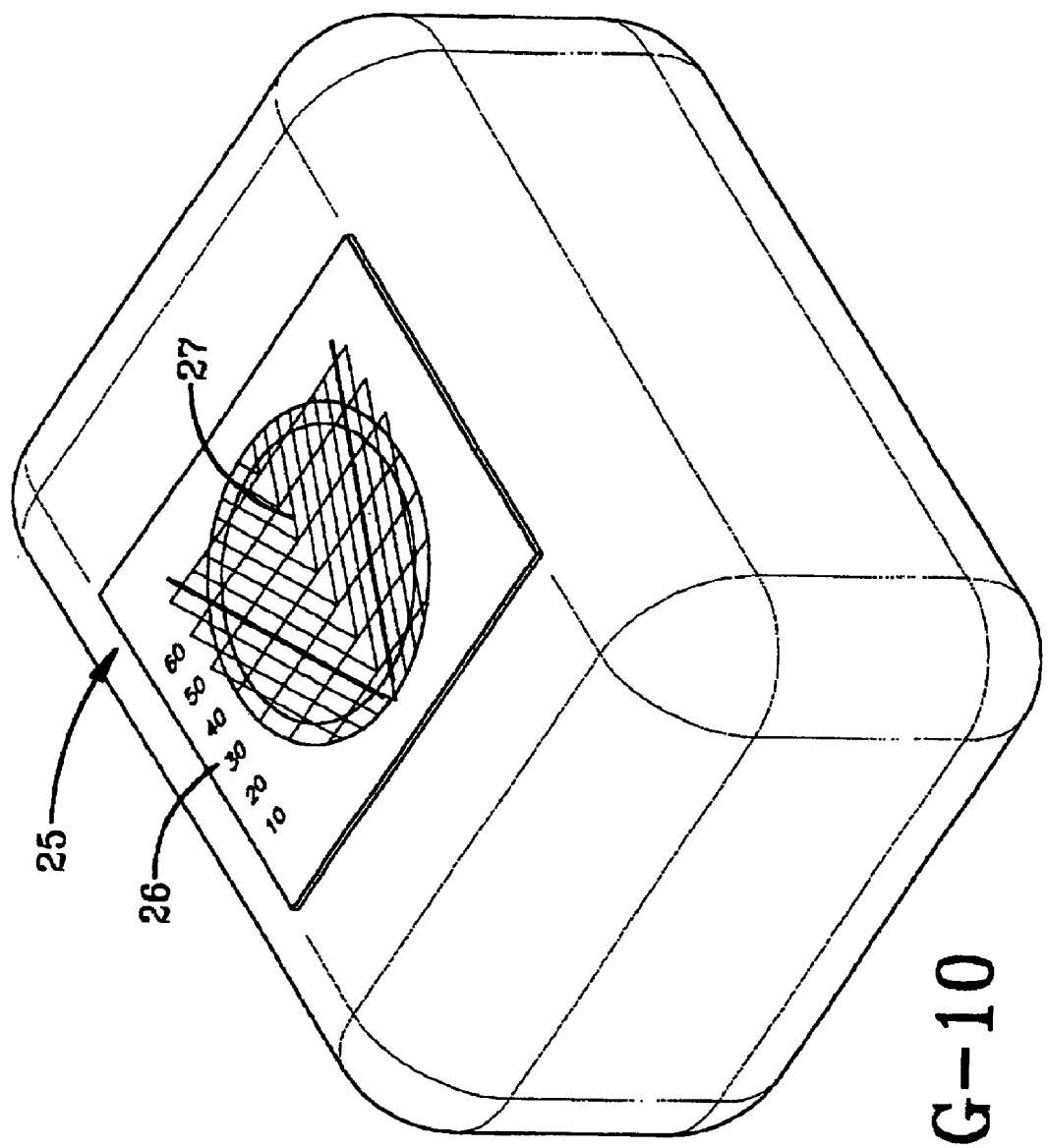
FIG. 10 is a perspective view of a lower template portion that may be used in accordance with one embodiment of the present invention.

FIG. 10 shows a closer view of the lower plane portion 25 with the lower plane template 26 that may be used to define the entry point.

Figure 11:
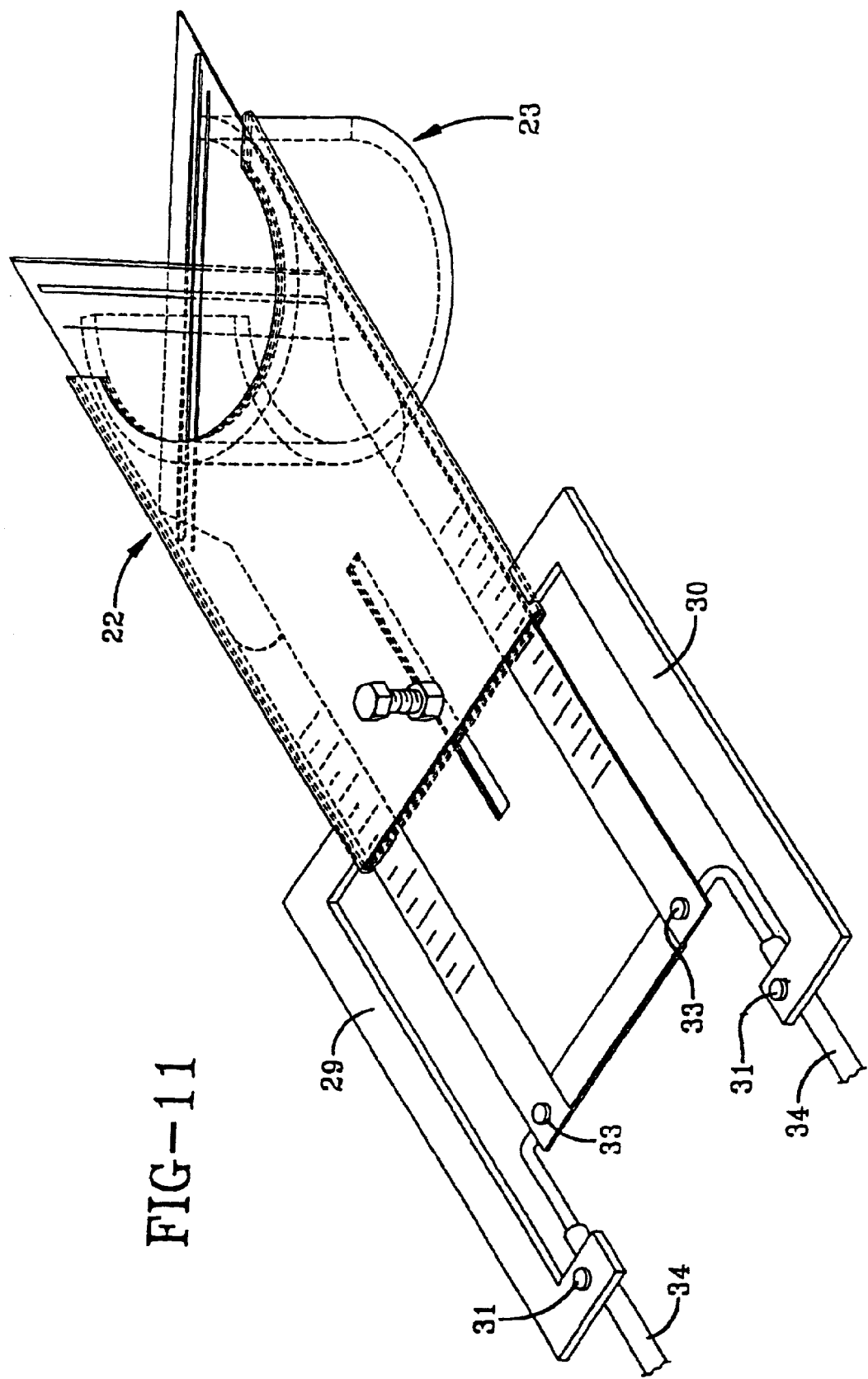
FIG. 11 is a perspective view of a remote-controlled stereotactic device that may be used in accordance with one embodiment of the present invention.

FIG. 11 shows remote actuators 34 attached to a stereotactic device of the present invention. In one such embodiment, a left bracket 29 and right bracket 30 are attached to the stereotactic device. The brackets may alternatively be one continuous piece, may be part of the sleeve, or may be unnecessary if the sleeve is designed with flaps or other attachment points for the controlling devices. A preferred bracket not only provides at least one rigid attachment point 31 for a cable or other remote-control device 34, but also acts to extend the rigid sleeve of the device. Each planar member preferably also provides an attachment point for an extending part 33 or other portion of the remote control device 34. The brackets and extending cable are preferably of a length to allow maximum travel distance for the angled portion of the movable planar members. These brackets allow adjustment of the stereotactic device from a distance away from the device, thereby allowing an operator to avoid any radiation or other potential hazard at or near the stereotactic device during operation.

In order to operate the device of the present invention, the following steps preferably may be followed for cross-sectional imaging pro0cedures:

1. The patient is imaged and the target is found.
2. A non-sterile pattern similar to or identical to the base component is placed on the skin approximately at the entry point.
3. Another image is acquired.
4. The relationship of the image plane to the pattern is measured.
5. If the pattern is not parallel then it is rotated based on the rotation correction scale.
6. Another image is made to confirm the pattern is parallel.
7. If parallel, then the entry point is found by drawing a vector on the computer screen.
8. The entry point location may be localized on the pattern and the skin may be marked (ink) at that point.
9. The skin preferably is prepared for sterile handling and treatment.
10. A sterile lower pattern is placed over the entry point parallel to the section plane. This is done by measuring the V1 and V2 image plane intersection distances to confirm that they are the same, if necessary.
11. The needle is pushed through the sterile base pattern at the desired entry specific point (for example where the distance on the pattern measures (14 mm)) and is then removed.
12. The skin may be numbed to anesthetize at the chosen point of entry.
13. The upper plane and intermediate frame portions are attached to the patient so that the chosen vector will be correct for the target, the entry point, and the upper component's range of motion, the needle is placed in the insertion point defined by the angled interwoven members in the upper plane.
14. The upper plane portion/intermediate frame portion combination is then placed in the corresponding lower plane portion ring and is oriented parallel to the image plane.
15. An image is acquired to confirm that everything is aligned.
16. The vector is drawn on the image through the needle entry point.
17. The first and/or second planar members are then moved to correct dimensions and directions to confirm that the needle is pointing at the target, by remote control.
18. The needle is then confirmed to be in the correct vector position outside the patient and the distance to the target is measured.
19. The needle may then be pushed to the target using local anesthetic.
20. The needle position in the target may then be confirmed by imaging.
21. The procedure is completed, such as through administration of medication or removing tissue for biopsy.
22. The needle is removed or the rest of the components are removed as desired.

In another example of the device's application, it may be used in conjunction with a fluoroscope. In fluoroscopy, the operator views the tissue and the target in the same fashion as watching a television. The lower pattern plane is not needed. The end of the probe (i.e., such as a needle) is positioned over the target live in real time. At this point, the skin may be anesthetized. The upper plane portion of the device is then placed over the target site (with the optional drape and support base). The probe is then placed at the target skin entry point and the upper plane portion would be aligned. The other end of the needle is placed in the alignment structure. Another fluoroscopic image is then acquired to find the target. By remote control, the planar members are manipulated until the probe is seen as just a dot (the probe at this point being parallel to the target vector). The lines of the pattern form a diamond around the target.

The fluoroscope can then be adjusted to a different angle and the operator can view the image in real time as the probe is advanced toward the target.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims, which are incorporated herein by reference.

What is claimed is:

1. A stereotactic device comprising:
   (a) a frame portion having an opening defining an upper alignment plane;
   (b) a first planar member comprising a first pair of substantially parallel image-conspicuous lines, said first planar member having a first slot disposed between said first pair of substantially parallel image-conspicuous lines;
   (c) a second planar member comprising a second pair of substantially parallel image-conspicuous lines, said second planar member having a second slot disposed a between said second pair of substantially parallel image-conspicuous lines;
   said first planar member overlying said second planar member such that said first pair of substantially parallel image-conspicuous lines forms an angle of about 53 degrees with said second pair of substantially parallel image-conspicuous lines, said first and second planar members adapted to move with respect to one another so as to be capable of providing an aperture, formed by the intersection of said first and second slots, at different positions within said upper alignment plane.

2. A stereotactic device according to claim 1 additionally comprising a lower plane portion comprising an image-conspicuous material defining at least one angle.

3. A stereotactic device according to claim 2 wherein said lower plane portion comprises a perforable material through which a medical instrument may be passed.

4. A stereotactic device according to claim 3 wherein said perforable material additionally comprises a graduated linear distance position scale.

5. A stereotactic device according to claim 2 wherein said lower plane portion additionally comprises a pair of adjacent angled patterns of an imager conspicuous material.

6. A stereotactic device according to claim 5 wherein said adjacent angled patterns define an angle of approximately 53 degrees.

7. A stereotactic device according to claim 2 wherein said lower plane portion additionally comprises an adhesive base portion.

8. A stereotactic device according to claim 2 wherein said lower plane portion is connected to an attachment band.

9. A stereotactic device according to claim 2 wherein said lower portion is attached to a drape material.

10. A stereotactic device according to claim 2 wherein said lower plane portion is connected to an attachment band, said attachment band being attached to a drape material.

11. A stereotactic device according to claim 1 wherein said first and second planar members are interwoven through said first and second slots.

12. A stereotactic device according to claim 1 wherein said first pair of substantially parallel image-conspicuous lines are of a different width than said second pair of substantially parallel image-conspicuous lines.

13. A stereotactic device according to claim 1 additionally comprising a sleeve for housing said first and second planar members, said sleeve capable of attaching to said frame portion.

14. A stereotactic device according to claim 13 wherein said sleeve contacts differing portions of said first and second planar members such that when said sleeve is pinched at certain locations one of said planar members is locked in place and only the other planar member may be moved with respect to said sleeve.

15. A stereotactic device according to claim 1 wherein said frame portion is adapted to rotate said first and second planar members with respect to an axis perpendicular to said first and second planar members.

16. A stereotactic device according to claim 15 wherein said frame portion additionally comprises a graduated position scale to indicate the degree of rotation of said first and second planar members.

17. A stereotactic device according to claim 1 additionally comprising at least one remote activator to move said first and second planar members.

18. A stereotactic device according to claim 17, wherein said at least one remote activator comprises a device to measure its movement, said device comprising:
   (a) a hollow sleeve,
   (b) a moveable member adapted to move within said sleeve, and
   (c) an engaging member extending into said hollow sleeve a sufficient distance to engage said moveable member so as to permit said moveable member to be moved within said hollow outer sleeve by a motion of said engaging member, and said engaging member disposed with respect to said moveable member so as to permit said moveable member to be moved discrete distances.

19. A stereotactic device according to claim 1 wherein substantially parallel image-conspicuous lines are selected from the group consisting of metal members, hollow polymeric members filled with an imager-conspicuous material, and polymeric members treated with an imager-conspicuous material.

20. A method of placing a probe or defining a vector from outside a tissue into a target area located within said tissue using an imaging device, said target area being within reach of said probe from a targeting surface of said tissue, said method comprising:
   (a) establishing a lower plane substantially at said surface of said tissue, said lower plane comprising a lower vector point;
   (b) establishing an upper alignment plane above said surface of said tissue, said upper plane comprising:
      (i) a first planar member comprising a first pair of substantially parallel image-conspicuous lines, said first planar member having a first slot disposed between said first pair of substantially parallel image-conspicuous lines;
      (ii) a second planar member comprising a second pair of substantially parallel image-conspicuous lines, said second planar member having a second slot disposed a between said second pair of substantially parallel image-conspicuous lines;

said first planar member overlying said second planar member such that said first pair of substantially parallel image-conspicuous lines forms an angle with said second pair of substantially parallel image-conspicuous lines, said first and second planar members adapted to move with respect to one another so as to be capable of providing an aperture, formed by the intersection of said first and second slots, at different positions within said upper line plane, said aperture of a dimension through which at least a portion of a medical instrument may be passed;

(c) if not so aligned, aligning said upper alignment plane such that the image plane of said imaging device is aligned perpendicular to the bisector of said angle formed by said substantially parallel image-conspicuous lines;

(d) determining the position of said aperture with respect to said lower vector point of said lower plane;

(e) adjusting said first and second planar members so as to form a vector containing said lower vector point, said aperture, and said target area; and (f) passing said probe along said vector to said target area.

* * * * *